United States Patent [19]

Yoshida et al.

[11] 4,245,122

[45] Jan. 13, 1981

[54] PROCESS FOR THE PRODUCTION OF ALLYL ACETONE

[75] Inventors: Takao Yoshida, West Long Branch; Denis E. Hruza, Sr., Brick Town; John B. Hall, Rumson, all of N.J.

[73] Assignee: International Flavors & Fragrances Inc., New York, N.Y.

[21] Appl. No.: 100,534

[22] Filed: Dec. 5, 1979

[51] Int. Cl.³ .............................................. C07C 45/45
[52] U.S. Cl. .................................. 568/397; 568/398; 568/877; 560/174
[58] Field of Search ............................. 260/595, 593 P

[56] References Cited

U.S. PATENT DOCUMENTS

| | | | |
|---|---|---|---|
| 3,609,192 | 9/1971 | Hoffman et al. | 260/595 |
| 3,914,289 | 10/1975 | Akutagawa et al. | 260/595 |
| 3,975,446 | 8/1976 | Kitagaki et al. | 260/595 |

OTHER PUBLICATIONS

Durst et al., J. Org. Chem., vol. 39, pp. 3271-3273 (1974).
Clark et al., J. Chem. Soc. Perkin I, 1977, pp. 1743-1745 (1977).
Matsumoto et al., Chem. Abst., vol. 90, #186769u (1979).
Purohit et al., Chem. Abst., vol. 90, #151516g (1979).
Sumitini et al., Chem. Abst., vol. 90, #151834j (1979).
House, Modern Synthetic Reactions, pp. 514-518 (1972).
Morrison et al., Organic Chemistry, pp. 937-938 (1966).

*Primary Examiner*—James H. Reamer
*Attorney, Agent, or Firm*—Arthur L. Liberman

[57] ABSTRACT

A process is described for the preparation of allyl acetone (5-hexen-2-one) according to the reaction:

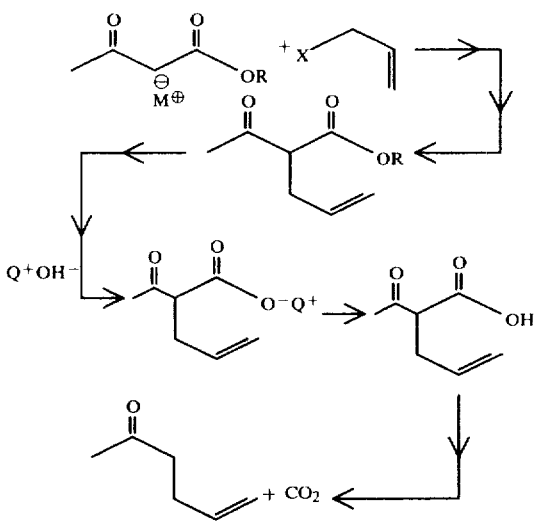

wherein R is methyl or ethyl; X is chloro or bromo; M is sodium or potassium; and Q is sodium or potassium, the reaction being carried out (i) using a phase transfer agent and (ii) in a two phase system.

2 Claims, 4 Drawing Figures

IR SPECTRUM FOR EXAMPLE II (ALLYL ACETONE)

PROCESS FOR THE PRODUCTION OF ALLYL ACETONE

BACKGROUND OF THE INVENTION

Allyl acetone having the structure:

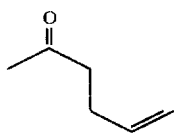

is a valuable substance useful as an intermediate in the formation of compounds valuable for use in perfumery such as, for example, the compound 1-(2,6,6-trimethyl-cyclohexen-1-yl)-1,6-heptadien-3-one which is produced from allyl acetone according to the reaction scheme:

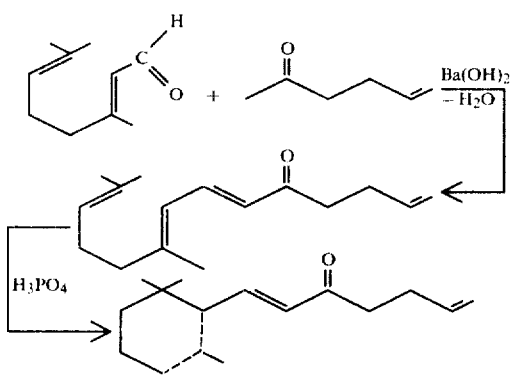

wherein the dashed lines signify a mixture of double bond isomers.

The instant invention describes a process for preparing allyl acetone by means of allylating an acetoacetic ester in the presence of (i) a phase transfer agent and (ii) in a two phase system.

In U.S. Pat. No. 4,010,207 a process is described for the preparation of substituted unsaturated aldehydes according to the reaction:

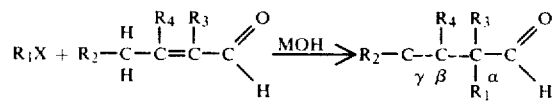

wherein one of the dashed lines is a double bond and the other of the dashed lines is a single bond; wherein $R_1$ is allyl or benzyl, $R_2$ is one of alkyl, aryl, alkenyl or alkoxyalkyl and $R_3$ and $R_4$ are each hydrogen or alkyl, with the proviso that when $R_3$ is alkyl the dashed line between the $\beta$ carbon atom and the $\gamma$ carbon atom represents a double bond and when $R_3$ is hydrogen, either of the dashed lines is a double bond, wherein X is chloro or bromo, and wherein M is alkali metal, the reaction being carried out (1) using a phase transfer agent, and (2) in a two phase system.

The instant reaction is different in kind from the reaction described and claimed in U.S. Pat. No. 4,010,207.

German Pat. No. 1,244,784, issued on July 20, 1967, discloses the reaction:

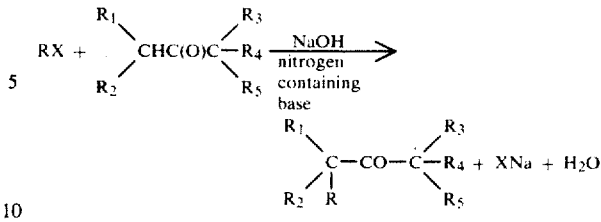

wherein R can be one of alkyl, alkenyl, allyl, propargyl, cyclohexyl or benzyl; X is chloro or bromo and $R_1$, $R_2$, $R_3$, $R_4$ and $R_5$ can be hydrogen, alkyl, alkenyl or phenyl. The reaction of the German Patent is limited to ketones. Although such ketones could be unsaturated, the nature of the reaction is different in kind from the reaction of the instant invention.

Chemical Abstracts, vol. 81 (1974) 135501 g, summarizes a paper by Tsukasa, et al. entitled: "Alkylation of alpha, beta-unsaturated cyclic ketones. Synthesis of jasmones". In this case cis and trans jasmones are synthesized by rection of 3-methyl-2-cyclopentenone with an alkyl halide in the presence of powdered potassium hydroxide and dimethyl sulfoxide; the Chemical Abstracts synthesis being carried out with dimethyl sulfoxide on a ketone rather than an aldehyde. This process is different in kind from the process of the instant invention.

In U.S. Pat. No. 4,045,489, issued on Aug. 30, 1977, a process is described for the preparation of cis-jasmone according to the reaction:

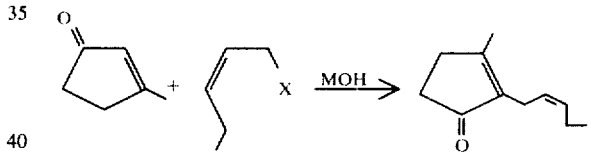

wherein X is chloro or bromo and wherein M is alkali metal, the reaction being carried out (1) using a "phase transfer agent" and (2) in a two phase system.

The reaction of the instant invention for the preparation of allyl acetone is different in kind from the reaction of U.S. Pat. No. 4,045,489, issued on Aug. 30, 1977.

U.S. Pat. No. 4,124,644, issued on Nov. 7, 1978, describes a process for the preparation of substituted oxyacetaldehydes and acetals thereof according to the reaction sequence:

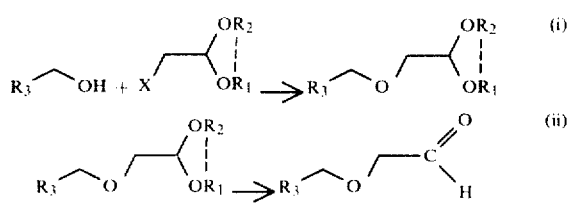

wherein $R_1$ and $R_2$ are each lower alkyl or $R_1$ and $R_2$, taken together form a lower alkylene group; wherein $R_3$ is alkyl, alkenyl or alkadienyl and X is halogen selected from the group consisting of chlorine and bromine, the reaction (i) being carried out (1) using a "phase transfer agent" and (2) in a two phase system.

The process of U.S. Pat. No. 4,124,644 is different in kind from the process for making allyl acetone of the instant invention.

In J. Org. Chem., Vol. 39, No. 22, 1974 at page 3271, an article by Durst & Liebeskind entitled, "Phase Transfer Catalysis. The Acetoacetic Ester Condensation" indicates that reaction of allyl chloride with methyl acetoacetate gives rise to a 30% yield of 4-carbomethoxy-1-hexen-5-one and reaction of methyl acetoacetate with allyl bromide in the presence of an Aliquat 336 ® catalyst gives rise to a 94.7% yield of 4-carbomethoxy-1-hexen-5-one. The reaction is carried out however in the presence of anhydrous benzene which gives rise to the danger of causing minute traces of benzene to exist in the final desired product which is to be used for its organoleptic properties in perfumery. The potential presence of such solvent is unacceptable in the perfumery field.

At page 4682 of J. Org. Chem., Vol. 43, No. 24, 1978 sodium and potassium carbonates are indicated to be useful as efficient strong bases in solid-liquid two phase systems in, for example, the alkylation of 9-substituted fluorene derivatives, thusly:

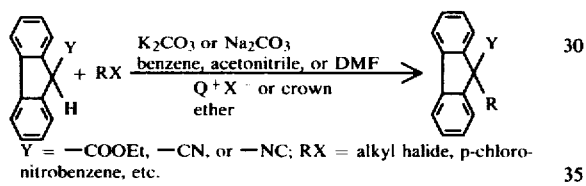

Y = —COOEt, —CN, or —NC; RX = alkyl halide, p-chloronitrobenzene, etc.

The Chemical Communications reference, however, does not suggest the use of sodium or potassium carbonates in a reaction such as the instant one. It is noteworthy that nowhere in the list of thirteen "starting" compounds is an allyl halide mentioned.

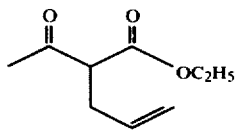

Figure 2:
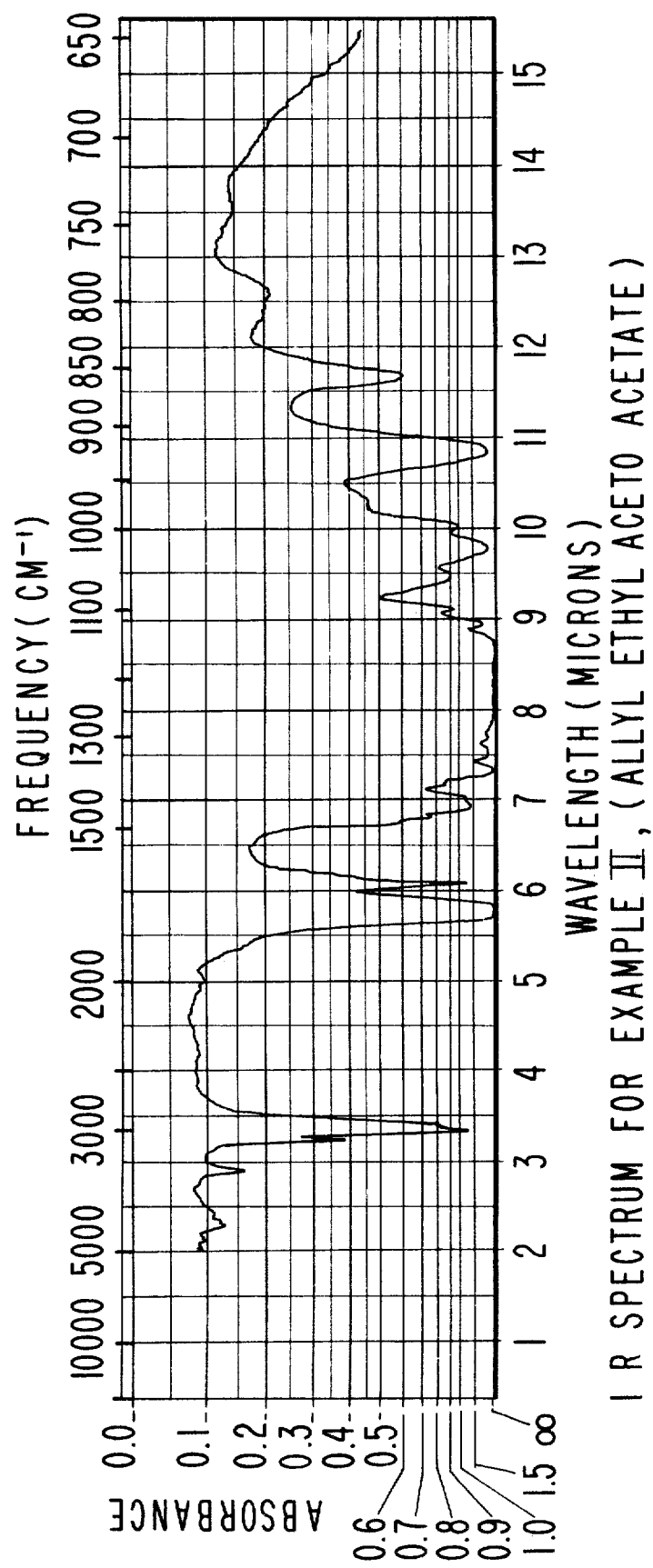

FIG. 2 is the infra-red spectrum for allyl ethyl aceto acetate having the structure:

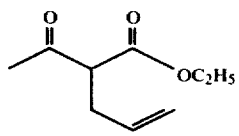

produced according to Example I.

Figure 3:
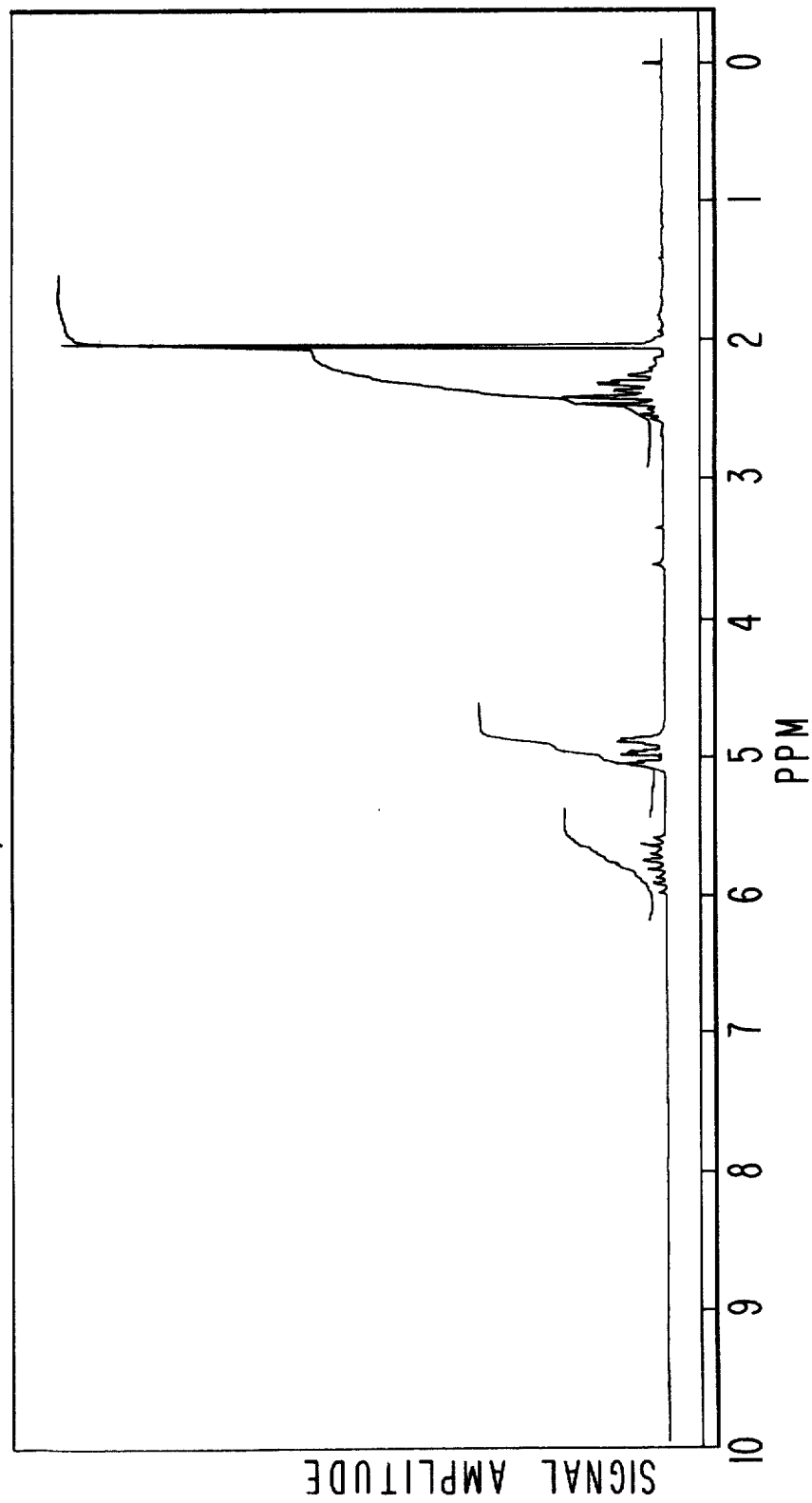

FIG. 3 is the NMR spectrum for allyl acetone having the structure:

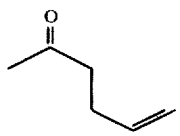

produced according to Example I.

Figure 4:
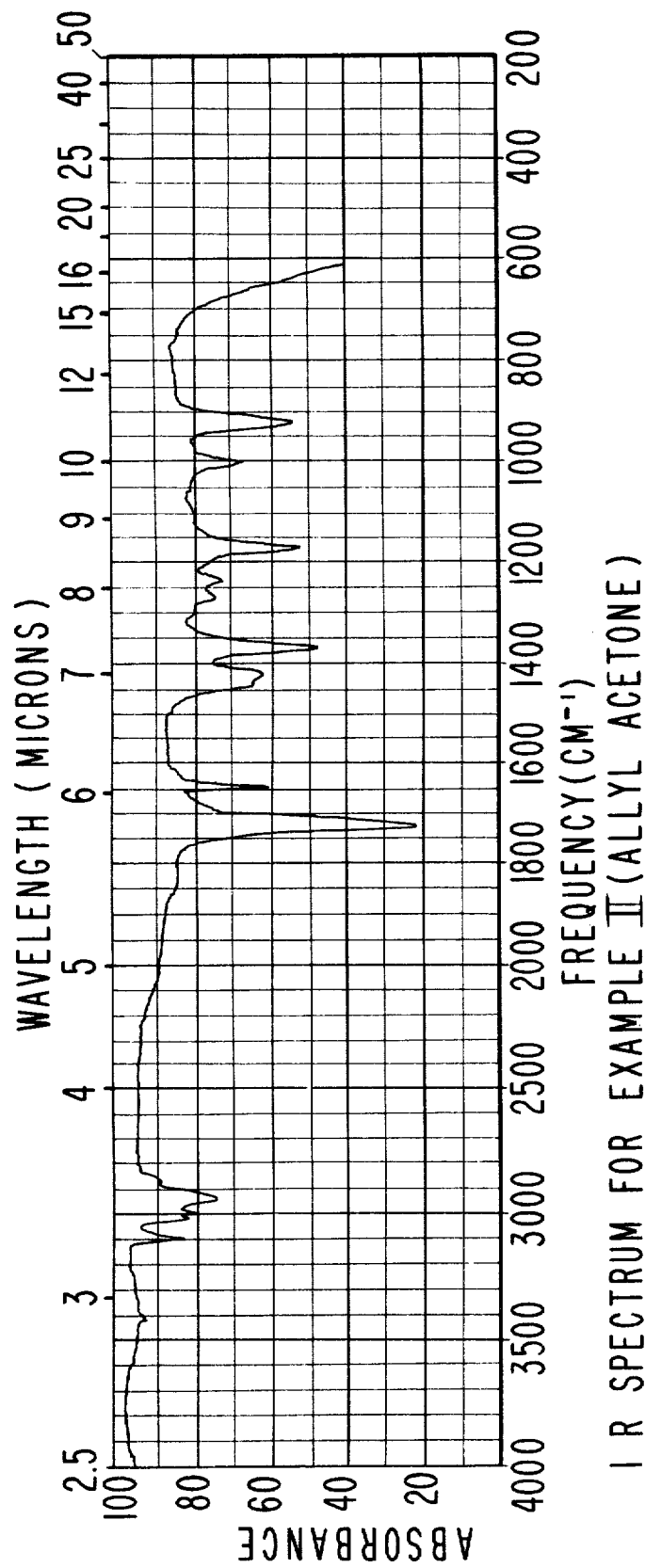

FIG. 4 is the infra-red spectrum for allyl acetone having the structure:

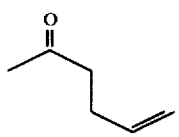

produced according to Example I.

OBJECT OF THE INVENTION

It is an object of this invention to produce allyl acetone having the structure:

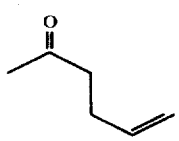

at such an efficiency and in such a yield as to make it practical for use as an intermediate in the perfumery industry for producing allyl beta ionone and allyl alpha ionone mixtures according to the process:

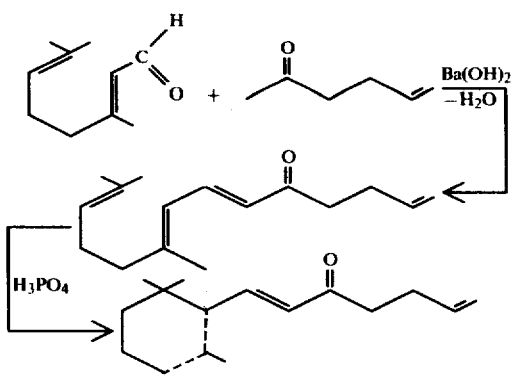

wherein the dashed lines signify a mixture of allyl beta ionone and allyl alpha ionone.

THE INVENTION

Described is a process for preparing allyl acetone according to the reaction sequence:

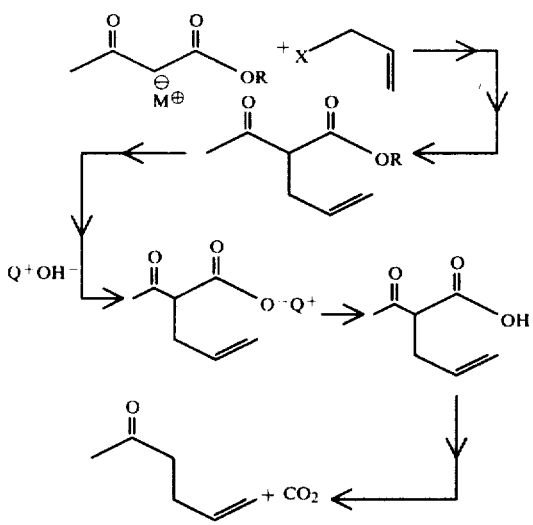

wherein R is methyl or ethyl; X is chloro or bromo; M is sodium or potassium; and Q is sodium or potassium, the reaction being carried out (i) using a phase transfer agent and (ii) in a two phase system.

More specifically, our invention provides a process for the allylation of acetoacetic ester; either a methyl ester or an ethyl ester under the influence of a base comprising the step of placing the reactants for the process and the base respectively in two immiscible phases; an organic phase and either (i) an aqueous base phase or (ii) a solid base phase with the reactants being located substantially entirely in the first mentioned organic phase and the base being located substantially entirely in the second mentioned phase; and adding to the two phase system a "phase transfer agent" which may be one or more of several organic quaternary ammonium salts.

Specific examples of "phase transfer agents" useful in our invention are as follows:

Tricapryl methyl ammonium chloride;
Cetyl trimethyl ammonium bromide; and
Benzyl trimethyl ammonium hydroxide.

In general, the "phase transfer agents" most preferred have the generic formula:

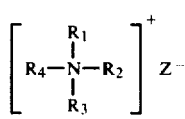

wherein at least one of $R_1$, $R_2$, $R_3$ and $R_4$ is $C_6$–$C_{14}$ aryl, $C_6$–$C_{10}$ aralkyl, $C_6$–$C_{20}$ alkyl, $C_6$–$C_{14}$ alkaryl and $C_6$–$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and Z- is an anion such as chloride, bromide and hydroxide.

The process of our invention is carried out in an inexpensive solvent which is inert to the reaction system such as toluene, benzene, o-xylene, m-xylene, p-xylene, ethyl benzene, n-hexane, cyclohexane, methylene chloride and o-dichlorobenzene or without solvent.

The process of our invention is carried out at a temperature in the range of from about 10° C. up to about 150° C. with a temperature range of 30°-120° C. being preferred. The reaction time is inversely proportional to the reaction temperature, with lower reaction temperature giving rise to greater reaction times; and, accordingly, the reaction time ranges from about 30 minutes up to about 10 hours.

In the reaction of our invention the mole ratio of the acetoacetic ester to allyl halide is in the range of from 0.5:1.5 up to about 1.5:0.5 with a preferred ratio of acetoacetic ester to allyl halide being from about 1:1 up to about 1:1.2.

The mole ratio of base to allyl halide in the reaction mass may be in the range of from about 0.75:1 up to about 1.5:1 with a preferred ratio of base:allyl halide being from about 1:1 up to about 1.2:1.

The quantity of phase transfer agent in the reaction mass based on amount of acetoacetic ester in the reaction mass may vary from 0.5 grams per mole of acetoacetic ester up to 25 grams of "phase transfer agent" per mole of acetoacetic ester with a preferred concentration of "phase transfer agent" being in the range of from about 2.5 up to about 7.5 grams of "phase transfer agent" per mole of acetoacetic ester.

The reaction of our invention is preferably carried out at atmospheric pressure since that is the most convenient condition. However, lower or higher pressures can be used without detrimentally affecting the ultimate yield of the desired product.

The particular base used in this reaction is indeed critical and, preferred, are sodium hydroxide and potassium hydroxide.

Most preferred are the bases sodium carbonate and potassium carbonate.

The following examples serve to illustrate embodiments of our invention as it is now preferred to practice it. It will be understood that these examples are illustrative and the invention is to be restricted thereto only as defined in the appended claims.

EXAMPLE I

PREPARATION OF ALLYL ACETONE

Reaction

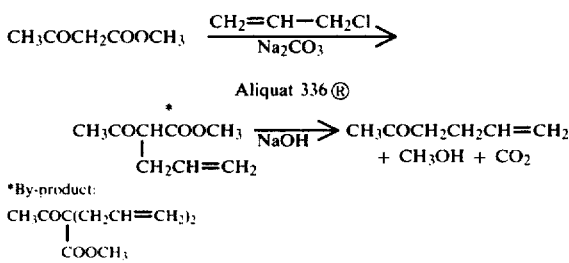

*By-product:

$$CH_3COC(CH_2CH=CH_2)_2$$
$$|$$
$$COOCH_3$$

Equipment 12-1, 3-neck flask
addition funnel
reflux condenser
thermometer
stirrer
Y-tube Reagent Methyl acetoacetate—2090 g (18 moles)
Sodium carbonate, anhydrous—1590 g (15 moles)
Allyl Chloride—1148 g (15 moles)
Aliquat 336 ®—170 g 50% Caustic soda—1500 g (18.8 moles)
Acetic Acid—2000 g

Procedure

Alkylation

1. Methyl acetoacetate (2090 g), sodium carbonate (1590 g) and Aliquat 336 ® (150 g) are placed in a 12-liter three neck reaction flask fitted with a reflux condenser, an addition funnel, a thermometer and a stirrer. No exotherm is observed.

2. Ice-cold water is circulated in the reflux condenser using a pump (Note 1).

3. The mixture is heated to 50° C. and allyl chloride (1148 g) is added over a period of 4 hours at 50° C. to 65° C. (exothermic) (Note 2).

4. After completion of adition of allyl chloride, the reaction mixture is heated gradually over a period of 3 hours to 100° C. maintaining a gentle reflux all the time (Note 3). At the end of this time GLC analysis indicates complete conversion of the allyl chloride.

5. The reaction mixture is cooled to 20°–25° C.

6. Water (5000 ml) is added to the reaction mixture and the mixture is stirred for 10 mins (Note 4).

7. In the other 12-liter reaction flask, acetic acid (1200 g) and water (1000 ml) are placed.

8. The reaction mixture obtained from Step 6 is poured into the aqueous acetic acid solution from Step 7 at 20°–25° C. Vigorous foaming takes place. Add very slowly with good agitation. (Note 5).

9. After settling, the organic layer is separated. The crude oil weighed 2743 g.

Hydrolysis and Decarboxylation

10. Water (5000 ml), 50% caustic soda (1500 g) and Aliquat 336 ® (20 g) are placed in a 12-liter reaction flask fitted with a reflux condenser, addition funnel, a thermometer, and a stirrer.

11. The mixture is heated to 50° C., and the crude oil obtained from Step 9 is added at 50° C. over a period of 1 hour (Note 6).

12. The reaction mixture is heated at 50°–80° C. for another two hours (Note 7).

13. After cooling the reaction mixture to room temperature the organic layer is separated.

14. The aqueous layer is acidified with acetic acid (800 g) and extracted with cyclohexane (400 g) (Note 8).

15. The oil layer obtained from the Step 13 and the cyclohexane extract are combined.

16. The crude oil is washed with saturated sodium bicarbonate (1000 ml) (Note 9) and saturated salt solution (1000 ml) (Note 9). The crude oil weighs 1963 g.

17. The washed crude oil is placed in a 3-liter distillation flask equipped with a Bidwell apparatus and a reflux condenser.

18. The mixture is heated under reflux until no more water is collected.

19. The dried crude oil is fractionated at atmospheric pressure using a 12"×1" Goodloe packed column with 50 g of Primol and 0.1 g of Ionox to give the following fractions.

| Fr. No. | Vapor Temp (°C.) | Liquid Temp (°C.) | Reflux Ratio | Weight (g) | Product[a] (g) |
|---|---|---|---|---|---|
| 1 | 65–78 | 91–112 | 2:1 | 182 | 4 |
| 2 | 78 | 112 | " | 133 | 4 |
| 3 | 78 | 112–131 | " | 144 | 7 |

-continued

| Fr. No. | Vapor Temp (°C.) | Liquid Temp (°C.) | Reflux Ratio | Weight (g) | Product[a] (g) |
|---|---|---|---|---|---|
| 4 | 78–128 | 131–138 | " | 167 | 127 |
| 5–7 | 128–129 | 138–165 | 0:1 | 488 | 471 |
| 8 | 129–166 | 165–214 | " | 181 | 170 |
| 9 | 166 | 214–230 | " | 45 | 7 |

Residue: 602 g
[a]Calculated by GLC analysis.
Chemical Yield: 790 g (54% of theory based on allyl chloride charged).
Acceptable Product: 669 g (Fr. 5–8, purity 96%) 58% wt/wt based on allyl chloride.

NOTE 1. To minimize the loss of allyl chloride from the system it is essential to use ice cold water (or IPA cooled with dry ice to 0°–10° C.) in the reflux condenser. In a large scale reaction it is suggested to use a caustic scrubber connected to the top of the reflux condenser.

2. Control the feed to have no more than a gentle reflux during the feeding time. Allyl chloride is considered to be a toxic compound (TLV=1 ppm), therefore, handling should be extremely careful. The top of the reflux condenser should be vented or scrubbed well during the entire reaction period.

3. For about 30 minutes no heat is necessary to keep a gentle reflux because of the reaction exotherm. The temperature reached ~70° C. After the exotherm had subsided the mixture is heated with a mantle heater.

4. Not all the salts will dissolve but the mass can be transferred into the quenching solution.

5. All solids should be dissolved. If not, add more water.

6. Carbon dioxide is released from the reaction. Add the crude oil slower than this rate if necessary.

7. At this time the intermediate (methyl allylacetoacetate) should be less than 1% on GLC analysis of the crude reaction mixture.

8. After acidification with acetic acid the pH value of the aqueous layer should be ~5. If not, add more acetic acid in 100 g increments.

9. The pH value of the aqueous layer should be ~7–8. If not, repeat the sodium bicarbonate wash.

EXAMPLE II

PREPARATION OF ALLYL ACETONE

Reaction $$CH_3COCH_2COOC_2H_5 \xrightarrow[Na_2CO_3]{CH_2=CH-CH_2Cl}$$

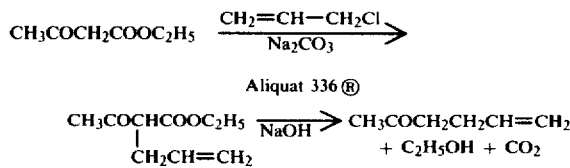

STEP A: Preparation of Ethyl-alpha-Allylacetoacetate

Into a 3 l, 3-neck flask equipped with air-driven stirrer, condenser with drying tube, thermometer, addition funnel with nitrogen bleed, dry-ice isopropanol bath and heating mantle are place 650 grams (5 moles) of ethyl acetoacetate, 530 grams (5 moles) of sodium carbonate, 383 grams (5 moles) of allyl chloride and 50 grams of Aliquat 336 ® (registered trademark of General Mills Chemical Company of Minneapolis, Minnesota for tricapryl methyl ammonium chloride). The mixture is heated to a temperature of between 70° C. and 105° C. for 3 hours.

2 liters of water is added to the reaction mass followed by addition of 500 grams of acetic acid in 1 liter of water.

The resulting mixture is placed in a 12 l flask, with acetic acid being added until the reaction mass is neutral. The reaction mass now exists in two phases: an aqueous phase and an organic phase. The aqueous phase is washed with 500 ml cyclohexane and the cyclohexane washings are combined with the organic phase. Resulting organic phase is then washed with 2 liters of saturated sodium chloride solution and the aqueous phase is re-extracted with cyclohexane.

STEP B: Preparation of Allyl Acetone

The resulting allyl ethyl acetoacetate/cyclohexane mixture is heated with 450 grams of 50% caustic soda to reflux for a period of 2 hours. After work-up in the same way as described in Example I, the crude oil was fractionated at atmospheric pressure to give a 53.6% yield of allyl acetone.

Figure 1:
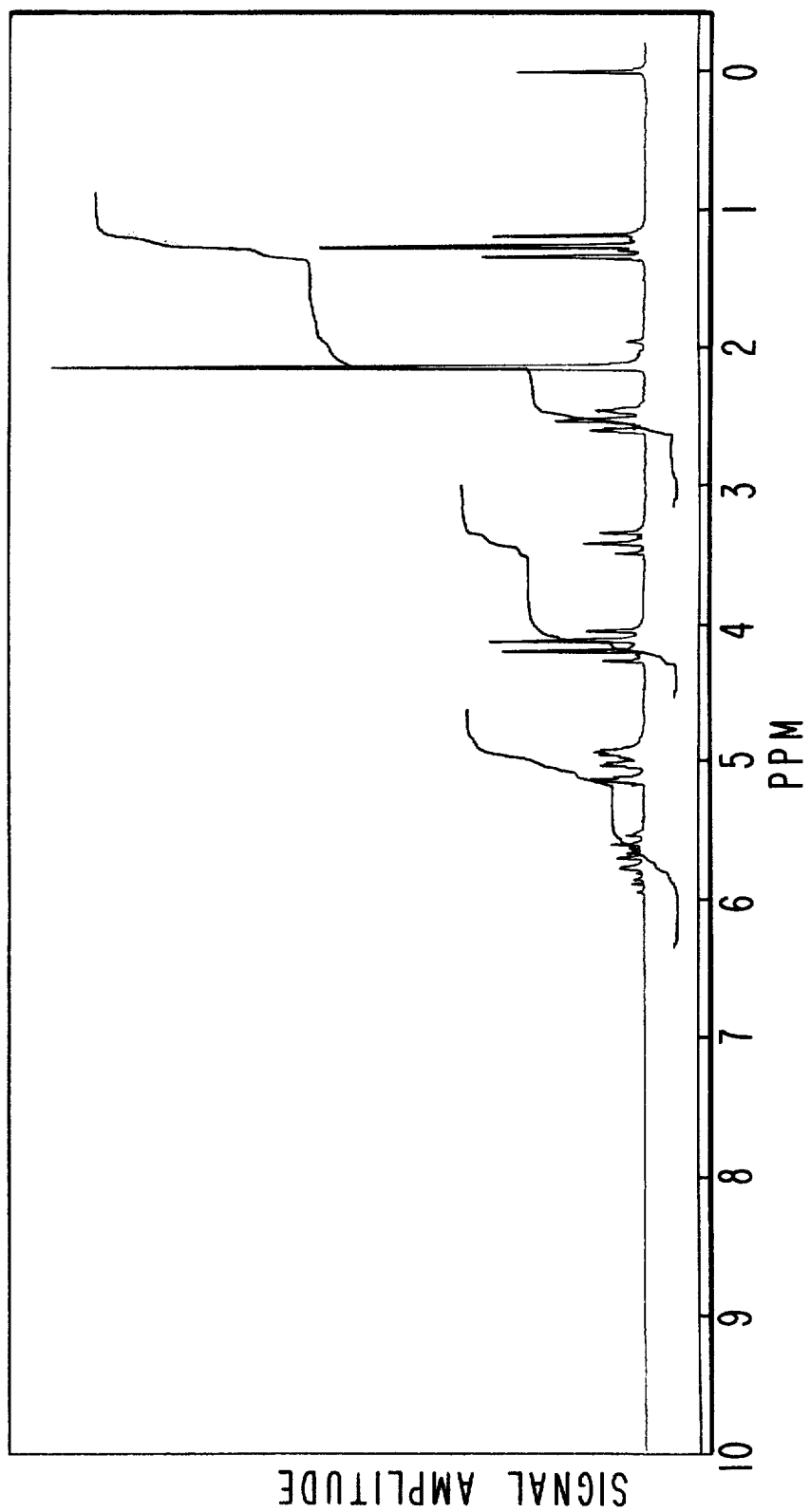
FIG. 1 is the NMR spectrum for allyl ethyl aceto acetate produced according to Example I, and having the structure.

FIG. 1 is the NMR spectrum for allyl ethyl acetoacetate produced above.

FIG. 2 is the infra-red spectrum for allyl ethyl acetoacetate produced above.

FIG. 3 is the NMR spectrum for allyl acetone produced above.

FIG. 4 if the infra-red spectrum for allyl acetone produced above.

EXAMPLE III

PREPARATION OF ALLYL ETHYL ACETOACETATE

Into a 500 ml reaction flask is placed 130 grams of ethyl acetoacetate; 138 grams of potassium carbonate; 10 grams of Aliquat 336 ®. The mixture is heated to 50° C. and 61 grams of allyl chloride (0.8 moles) is added. The heating is continued for a period of 2 hours after which time the reaction mass is worked up by means of the same procedure as Example I, and the allyl ethyl acetoacetate is produced in 30% of theory.

EXAMPLE IV

PREPARATION OF ALLYL METHYL ACETOACETATE

A reaction is carried out in the same manner as in Example III with the exception that methyl acetoacetate is used as a reactant instead of ethyl acetoacetate. The resulting product, allyl methyl acetoacetate, is produced in 66% yields.

EXAMPLE V

PREPARATION OF ALLYL ACETONE

Reactions

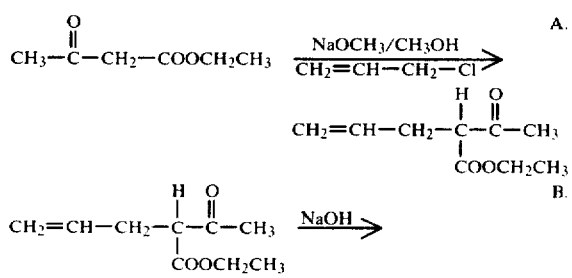

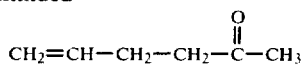

STEP A: Preparation of Ethyl-alpha-allyl-acetoacetate

Equipment 12-l, 3-neck flask
air-driven stirrer
condenser with drying tube
thermometer
addition funnel with nitrogen bleed
dry-ice isopropanol bath
heating mantle Materials 25% sodium methoxide in methanol—3425 g
ethyl acetoacetate—2145 g (16.5 moles)
allyl chloride—1155.5 g (15 moles)
glacial acetic acid—200 ml Procedure 25% sodium methoxide in methanol (3425 g) is placed in flask and cooled to 20° C. Then 2145 g ethyl acetoacetate is added over a ½-hour period maintaining the reaction temperature 20°–25° C. with external cooling. The reaction mixture is then stirred at 20° C. for ½-hour and 1155.5 g allyl chloride is added dropwise with stirring over ½-hour period gradually letting the pot temperature rise. The reaction mixture is heated to reflux and held there two hours (pot temperature 62°–68° C.). The reaction mixture is cooled to 60° C. and neutralized to pH=7 with 200 ml glacial acetic acid. The solvent is then stripped off using a 6" column with Protruded Packing. The distillation is continued until the pot temperature reaches 80° C.; 2910 g solvent is collected. The reaction mixture is cooled and diluted with 2 liters of water. The upper oil layer is separated (2570 g).

STEP B: 5-Hexen-2-one

Equipment 12-l, 3-neck flask
air-driven stirrer
condenser
thermometer
heating mantle Materials crude oil (Step A)—2570 g
50% sodium hydroxide (U.B. Plant)—1440 g
glacial acetic acid—250 ml
benzene—1 liter
10% salt solution—1 liter Procedure The crude oil layer is added to 1440 g 50% sodium hydroxide solution diluted with 6 liters of water and refluxed for 1½ hours. The reaction mixture is cooled to room temperature, and the upper organic layer is separated off. The lower aqueous layer is acidified with 250 ml glacial acetic acid and extracted with one 1-liter portion of benzene. The benzene extract is washed with one 1-liter portion of 10% aqueous sodium chloride solution. The combined organic layers are rushed over in an atmospheric distillation using a 6" column Protruded Packing. The product distills at 126°–131° C. yielding 741 g or 50.4% theoretical.

Analytical Data

Mass Spectrum—98/43, 27, 55, 39, 29, 41, 26.

The major impurity in the product is benzene. Redistillation using a 12" column with Protruded Packing and monitoring by GLC affords a product containing <5% benzene and nil water content.

Table I summarizes the experimental data obtained for the preparation of allyl acetone by the alkylation of acetoacetic ester with allyl chloride in the presence of sodium or potassium carbonate and phase transfer reagents.

An initial trial run (Run 1) for alkylation of ethyl acetoacetate with allyl chloride in the presence of potassium carbonate and Aliquat 336 ® as a phase transfer catalyst at 50° C. for 2 hours gives about 30% chemical yield of ethyl allyl acetoacetate by GLC analysis based on allyl chloride charged. Attempts to increase the yield of the alkylated aceto acetate using potassium carbonate by increasing the reaction time and temperature are unsuccessful (Run 2 and 3).

However, using sodium carbonate as base in place of potassium carbonate, the yield of alkylated product improves to ~45% (by GLC) (Run 4). In this experiment all reagents, ethyl acetoacetate (1.0 mole), sodium carbonate (1.0 mole), allyl chloride (0.8 moles) and Aliquat 336 ® (10 g) are placed in the reaction flask, and the mixture is heated from 50° C. to 118° C. over a period of 1 hour, when the GLC analysis using decane as an internal standard shows ~45% chemical yield of ethyl acetoacetate with two byproducts, ethyl diallyl acetoacetate (~6%) and an unknown with a molecular weight of 170 (~2%). A similar reaction using polyoxyethylene as a phase transfer catalyst does not give any product (Run 5). In Run 6 the reaction is scaled up to 5 moles scale under the conditions of Run 4 except the reaction time is increased to 4 hours (from 1 hour in Run 4).

After 4 hours of aging only ~1% of allyl chloride is left in the reaction mixture. The reaction mixture is worked up and a 66% chemical yield of allyl ethyl acetoacetate based on allyl chloride charged together with ~6% of ethyl diallyl acetoacetate and ~2% of the unknown is obtained. This experiment is repeated (Run 7) giving a 67% chemical yield of ethyl allyl acetoacetate which is further converted to allyl acetone by hydrolysis and decarboxylation. Thus, the crude oil is added to a 10% caustic soda solution at 40°–50° C. over 15 minutes and the reaction mixture is stirred at 50°–80° C. for 1 hour. After distillation using 12" Goodloe packed column, allyl acetone is obtained in a chemical yield of 54% based on allyl chloride charged by the GLC analysis on the fractions, and 93% pure allyl acetone is obtained in 63% wt/wt yield based on allyl chloride charged.

An attempt to hydrolyze and decarboxylate the ethyl allyl acetoacetate under acidic conditions using sulfuric acid is unsuccessful (Run 8).

The subsequent experiments are carried out to establish the procedure using methyl acetoacetate. Run 9 is carried out under the same conditions as in Run 7 but using methyl acetoacetate instead of ethyl acetoacetate.

The yield of methyl allyl acetoacetate is 55% by GLC analysis on the crude reaction mixture. This material is further hydrolyzed and decarboxylated with 17% caustic soda to give a chemical yield of 51% (Run 10) after distillation. In Run 11 the amount of sodium carbonate is reduced to 60 mole % from 100 mole % based on allyl chloride, but for some reason the reaction mixture becomes excessively thick during the reaction. The chemical yield of methyl allyl acetoacetate is ~50% by GLC analysis on the crude reaction mixture. Repeat of this reaction (Run 12) gives almost the same yield (51%), which is lower than with the use of 100 mole % of sodium carbonate, but without any problem of thickening. Therefore, the amount of sodium carbonate is fixed at 100 mole % based on allyl chloride. While conducting these experiments a mild exotherm is observed during the early stage of the reaction. The heat of reaction is approximately −42 Kcal/g-mole; suggesting a moderately high exothermic reaction. This indicates the necessity of adjusting the allyl chloride feed to the rate of reaction and the cooling capacity of the reactor in order to avoid the potentially hazardous accumulation of unreacted allyl chloride. Thus, in Runs 13 and 14 allyl chloride is added to a mixture of methyl acetoacetate, sodium carbonate and Aliquat 336 ® over a period of 2–2.5 hours at 85°–95° C. in Run 13 and 90°–112° C. in Run 14, expecting a faster reaction rate at the higher temperature, followed by aging at 95°–98° C. for 1 hour in Run 13 and at 42°–46° C. for 1.5 hours in Run 14.

However, the control of the allyl chloride addition is difficult because of occasional flooding of refluxing allyl chloride in the condenser. The chemical yield of methyl allyl acetoacetate based on allyl chloride is 40% in Run 13 and 50% in Run 14. The lower yields may be due to the loss of allyl chloride from the condenser during the addition. Therefore, in Run 15, allyl chloride is added to a mixture of methyl acetoacetate, sodium carbonate, and Aliquat 336 ® at 45° C. over a period of 1 hour and the reaction mixture is stirred for 10 hours at 45°–65° until the maximum yield of methyl allyl acetoacetate is obtained GLC analysis. During the first hour of this aging period occasional cooling is necessary to control the reflux of allyl chloride, but after the exothermic reaction subsides, heating is necessary to maintain the temperature at 65° C. The chemical yield of allyl acetone is 43% of theory based on allyl chloride after distillation.

To control the exothermic reaction better during and after the allyl chloride addition the addition time is lengthened to 3 hours (at 45°–70° C.) in Run 16 during which time a gentle reflux of allyl acetone is maintained by the heat generated from the reaction itself. Then the reaction mixture is stirred and heated at 70°–96° C. for 7 hours under a gentle reflux. However, after 7 hours aging GLC analysis shows ~3% of unreacted allyl chloride remaining in the reaction mixture, and no further increase in methyl allyl acetoacetate is observed. A chemical yield of 65% of methyl allyl acetoacetate by GLC analysis on the crude reaction mixture is obtained.

The yield of allyl acetone is 54% after hydrolysis and decarboxylation. To have unreacted allyl chloride is not desirable from the standpoint of the exposure hazard involved in large scale operations (TLV for allyl chloride is 1 ppm). Therefore, the amount of methyl acetoacetate is increased to 120 mole % against allyl chloride in Runs 17–19 to insure the complete conversion of allyl chloride. At the end of the aging period the level of allyl chloride is nil to <1% in these experiments. In Run 18 a much longer addition time (19 hours at 45°–50° C.) is applied, but no significant change in the yield of allyl acetone is observed, namely 53% in Run 17 and 54% in Run 18.

The final conditions are established in Run 19 (see Example I). A chemical yield of 63% of theory based on allyl chloride is obtained. This is the highest yield obtained among all experiments done.

(g) fractionally distilling the resulting reaction product yielding substantially pure allyl acetone.

The mole ratio of sodium carbonate:allyl chloride:ethyl or methyl acetoacetate being about 1:1:1; and the ratio of tricapryl ammonium chloride:allyl chloride being about 10 grams per mole, the reaction of the allyl chlo-

TABLE I
ALLYL ACETONE

| | REAGENT (MOLE) | | | | | | YIELD (%) | |
|---|---|---|---|---|---|---|---|---|
| | 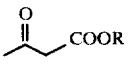<br>R = C$_2$H$_5$ Runs 1-7<br>R = CH$_3$ Runs 9-19 |  | | | REACTION$^e$ | REACTION$^e$ | 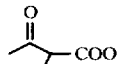 | 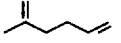 |
| RUN | | | BASE | Aliquat 336®(g) | Temp. (°C.) | Time (hr) | | |
| 1 | 1.0 | 0.8 | K$_2$CO$_3$, 1.0 | 10 | 50 | 2 | ~30 $^a$ | |
| 2 | 1.0 | 0.8 | K$_2$CO$_3$, 1.0 | 10 | 75-88 | 7.5 | ~26 $^a$ | |
| 3 | 1.0 | 0.8 | K$_2$CO$_3$, 1.0 | 10 | 80-103 | 9.5 | 18 $^a$ | |
| 4 | 1.0 | 1.0 | Na$_2$CO$_3$, 1.0 | 10 | 50-118 | 1 | 45 $^a$ | |
| 5 | 1.0 | 1.0 | Na$_2$CO$_3$, 1.0 | (10 $^d$) | 70 | 4 | 0 | |
| 6 | 5.0 | 5.0 | Na$_2$CO$_3$, 5.0 | 50 | 67-104 | 4 | 66 $^a$ | |
| 7 | 5.0 | 5.0 | Na$_2$CO$_3$, 5.0 | 50 | 70-105 | 3 | 67 $^a$ | 54 $^b$ |
| 8 | (Hydrolysis of Run 6 using 50% H$_2$SO$_4$) | | | | 100 | | | ~10 $^b$ |
| 9 | 5.0 | 5.0 | Na$_2$CO$_3$, 5.0 | 50 | 55-109 | 2.5 | 55 $^a$ | |
| 10 | (Hydrolysis of Run 9 using 17% NaOH) | | | | 81-82 | 2.0 | | 51 $^b$ |
| 11 | 5.0 | 5.0 | Na$_2$CO$_3$, 3.0 | 50 | 25-90 | 12.0 | ~50 $^{a,c}$ | |
| 12 | 5.0 | 5.0 | Na$_2$CO$_3$, 3.0 | 50 | 25-80 | 4.0 | 51 $^a$ | |
| 13 | 5.0 | 5.0 | Na$_2$CO$_3$, 5.0 | 50 | (85-95)95-98 | (2.0)1.0 | 40 $^a$ | |
| 14 | 15.0 | 15.0 | Na$_2$CO$_3$, 15.0 | 150 | (90-112)42-46 | (2.5)1.5 | 50 $^a$ | |
| 15 | 15.0 | 15.0 | Na$_2$CO$_3$, 15.0 | 120 | (45)45-65 | (1.0)10.0 | 60 $^a$ | 43 $^b$ |
| 16 | 15.0 | 15.0 | Na$_2$CO$_3$, 15.0 | 150 | (45-70)70-96 | (3.0)7.0 | 65 $^a$ | 54 $^b$ |
| 17 | 18.0 | 15.0 | Na$_2$CO$_3$, 15.0 | 150 | (50-80)80-100 | (4.0)6.0 | 69 $^a$ | 53 $^b$ |
| 18 | 18.0 | 15.0 | Na$_2$CO$_3$, 15.0 | 150 | (45-50)50-102 | (19.0)3.0 | 78 $^a$ | 54 $^b$ |
| 19 | 18.0 | 15.0 | Na$_2$CO$_3$, 15.0 | 150 | (50-65)65-100 | (4.0)3.0 | | 63 $^b$ |

$^a$ Calculated by GLC analysis on the crude reaction mixture.
$^b$ Calculated by GLC analysis on the distilled materials.
$^c$ The reaction mixture became very thick.
$^d$ Polyoxyethylene (Av. mole wt. 100,000 ex Aldrich) was used as a phase transfer reagent.
$^e$ The reaction temperature and time are for the aging period. In Run 13-19 the numbers in parenthesis are for the temperature and time for allyl chloride addition. In Run 1-12 all reagents were combined and heated at the conditions described.

What is claimed is:

1. A process for preparing allyl acetone comprising the steps, in sequential order of:
   (a) first mixing methyl acetoacetate or ethyl acetoacetate with sodium carbonate and tricapryl methyl ammonium chloride;
   (b) heating the mixture to a temperature in the range of about 50° C.;
   (c) adding allyl chloride to the resulting mixture while maintaining the temperature of the reaction mass in the range of from about 50° C. up to about 65° C.;
   (d) heating the reaction mass slowly to a temperature of about 100° C. over a period of three hours;
   (e) cooling the reaction mass to a temperature in the range of 20°-25° C.;
   (f) hydrolyzing the resulting reaction product using aqueous acetic acid at a temperature in the range of 20°-25° C.;

ride and methyl or ethyl acetoacetate taking place in the absence of solvent.

2. A process for preparing allyl acetone comprising the step of intimately admixing ethyl or methyl acetoacetate, sodium carbonate, allyl chloride and tricapryl ammonium chloride, heating the resulting mixture to a temperature in the range of 50°-118° C. for a period of from one up to four hours; then cooling the reaction mass to a temperature in the range of 20°-25° C. and intimately admixing the reaction mass with aqueous acetic acid whereby the allyl aceto acetic ester is hydrolyzed; then distilling the resulting allyl acetone whereby substantially pure allyl acetone is produced; the mole ratio of allyl chloride:sodium carbonate:ethyl or methyl aceto acetic ester being about 1:1:1 and the ratio of tricapryl methyl ammonium chloride:allyl chloride being about 10 grams per mole, the reaction of the allyl chloride and methyl or ethyl acetoacetate taking place in the absence of solvent.

* * * * *